United States Patent
Henderson et al.

(10) Patent No.: US 8,569,402 B2
(45) Date of Patent: *Oct. 29, 2013

(54) MOULDABLE BIODEGRADABLE POLYMER

(75) Inventors: Rulande Henderson, Portland, OR (US); Ian John Partridge, Melton (AU); Elizabeth Emily Rose, Elsternwick (AU); Nicholas Roy Oakley, Lara (AU)

(73) Assignee: Plantic Technologies Ltd., Altona, Victoria (AU)

( * ) Notice: Subject to any disclaimer, the term of this patent is extended or adjusted under 35 U.S.C. 154(b) by 904 days.

This patent is subject to a terminal disclaimer.

(21) Appl. No.: 11/664,649

(22) PCT Filed: Oct. 5, 2005

(86) PCT No.: PCT/AU2005/001507
§ 371 (c)(1),
(2), (4) Date: Jul. 27, 2007

(87) PCT Pub. No.: WO2006/037157
PCT Pub. Date: Apr. 13, 2006

(65) Prior Publication Data
US 2007/0276317 A1    Nov. 29, 2007

(30) Foreign Application Priority Data

Oct. 5, 2004   (AU) ................. 2004905695

(51) Int. Cl.
*D21H 19/58*     (2006.01)
(52) U.S. Cl.
USPC ............. 524/52; 428/500; 428/522; 428/532; 524/47; 524/386; 524/387; 524/388; 524/389; 604/15
(58) Field of Classification Search
USPC ........ 524/47, 52, 386, 387, 388, 389; 604/15; 428/500, 522, 532
See application file for complete search history.

(56) References Cited

U.S. PATENT DOCUMENTS

| | | |
|---|---|---|
| 5,234,977 A | 8/1993 | Bastioli et al. |
| 5,316,578 A | 5/1994 | Buehler et al. |
| 5,350,354 A | 9/1994 | Billmers |
| 5,393,804 A | 2/1995 | George et al. |
| 5,462,981 A | 10/1995 | Bastioli et al. |
| 5,500,465 A * | 3/1996 | Krishnan et al. ............... 524/47 |
| 5,512,090 A | 4/1996 | Franke et al. |
| 5,902,262 A * | 5/1999 | Bastioli et al. ................ 604/1 |
| 6,231,970 B1 | 5/2001 | Andersen et al. |
| 6,277,899 B1 | 8/2001 | Bastioli et al. |
| 6,730,057 B2 | 5/2004 | Zhao et al. |
| 6,821,590 B2 * | 11/2004 | Verrall et al. ............... 428/35.7 |
| 2002/0042599 A1 * | 4/2002 | Zhao et al. .................. 604/367 |
| 2003/0036721 A1 * | 2/2003 | Zhao et al. ................... 604/15 |
| 2004/0122135 A1 | 6/2004 | Halley et al. |
| 2004/0242732 A1 | 12/2004 | Yu et al. |

FOREIGN PATENT DOCUMENTS

| | | | |
|---|---|---|---|
| EP | 0 613 672 A1 | 9/1994 | |
| EP | 0 635 645 A2 | 1/1995 | |
| EP | 0 954 422 B1 | 11/1999 | |
| WO | WO 92/16583 A1 | 10/1992 | |
| WO | WO 9219680 A1 * | 11/1992 | ............... C08L 3/02 |
| WO | WO 02/074352 * | 9/2002 | |

OTHER PUBLICATIONS

International Preliminary Report on Patentability and International Search Report for PCT/AU2005/001507, dated Mar. 8, 2007, 11 pages.

* cited by examiner

*Primary Examiner* — David W Wu
*Assistant Examiner* — Marie Reddick
(74) *Attorney, Agent, or Firm* — Kilyk & Bowersox, P.L.L.C.

(57) ABSTRACT

A biodegradable injection moldable polymer having the composition a) from 50 to 85% by weight of a starch and or a modified high amylose starch b) from 4 to 13% by weight of a water soluble polymer selected from polyvinylacetate, polyvinyl alcohol and copolymers of ethylene and vinylalcohol which have a melting point compatible with the molten state of the starch components c) from 10 to 35% by weight of a polyol plasticizer d) from 0.5 to 10% of a polyethylene oxide or polyethylene glycol e) from 0 to 1.5% by weight of a $C_{12-22}$ fatty acid or salt and f) from 0.25% to 3% of a food grade emulsifier. The polymers are suitable for biodegradable, flushable tampon applicators and other medical or industrial products where flushability and bio degradability are desirable.

17 Claims, 3 Drawing Sheets

MOULDABLE BIODEGRADABLE POLYMER

This application is a National Stage Application of PCT/AU2005/001507, filed Oct. 5, 2005.

This invention relates to improvements in biodegradable polymeric products particularly injection mouldable starch based polymers.

BACKGROUND TO THE INVENTION

There is an increasing demand for many plastic products to be biodegradable. One product that has been the subject of attention is the tampon applicator which conveniently should be water flushable water dispersible and biodegradable. Difficulties have been encountered in producing starch based polymers particularly for injection moulding. The molecular structure of the starch is adversely affected by the shear stresses and temperature conditions needed to plasticise the starch and pass it through the extrusion die. For most products foaming has to be avoided and this generally requires attention because of the water content of the starch. Foaming has been avoided by degassing the melt prior to exiting the die as suggested in U.S. Pat. Nos. 5,314,754 and 5,316,578. The latter patent also avoids adding water to the starch. As explained in U.S. Pat. No. 5,569,692 by not drying starch and avoiding the addition of water the starch can be processed at temperatures between 120° C. and 170° C. because the water bound to the starch does not generate a vapour pressure such as to require high pressures.

Another approach to improving the melt processability of starch is to provide an additive as in U.S. Pat. No. 5,362,777 which reduces the melting point of the starch. The additive is selected from dimethyl sulfoxide, a selection of polyols and amino or amide compounds.

U.S. Pat. No. 5,043,196 discloses a high amylose starch for injection moulding.

U.S. Pat. No. 5,162,392 to an injection moldable corn starch and LDPE biodegradable polymer.

In order to produce starch polymers for particular applications they have been blended with a range of other polymers. Biodegradable blown films are disclosed in U.S. Pat. No. 5,322,866 which blends raw starch, polyvinyl alcohol and talc with glycerol and water. U.S. Pat. No. 5,449,708 discloses compositions of starch ethylene acrylic acid and a salt of stearic acid plus a glycerol based lubricant. Flexible and clear transparent sheets are disclosed in U.S. Pat. No. 5,374,304. These are composed of a high amylose starch and a glycerol plasticizer. The use of starch in conjunction with high amylose or modified starches has also been proposed. U.S. Pat. Nos. 5,314,754, and 5,316,578 both suggest the use of modified starches including hydroxypropyl substituted starches. Hydroxypropylation reportedly increases elongation at break and burst strength and improved resilience in the polymers.

Patent WO00/36006 discloses biodegradable water soluble formulations using a major amount of modified starch and a minor amount of a water soluble poly vinyl alcohol. These formulations are thermo formable but there are no examples of injection mouldable compositions.

Biodegradable tampon applicators are the subject of a number of patents. U.S. Pat. No. 5,759,569 discloses trans polyisoprene as biodegradable polymer for diaper top sheets and tampon applicators.

Patent applications 2003/0036721 and 2003/0040695 relate to flushable tampon applicators comprised of polyethylene oxides and other components.

U.S. Pat. No. 5,002,526 discloses a polyvinyl alcohol tampon applicator.

U.S. Pat. No. 5,350,354 discloses a tampon applicator composed of starch or modified starch, at least 5% of a plasticizer such as glycerol and water.

U.S. Pat. No. 5,804,653 to a moldable polyvinyl alcohol composition for tampon applicators.

It is an object of this invention to provide an injection mouldable biodegradable polymer which can be processed have acceptable properties for intended uses such as tampon applicators.

BRIEF DESCRIPTION OF THE INVENTION

The present invention provides a biodegradable injection mouldable polymer having the composition on a dry weight basis of
- a) from 50 to 85% by weight of a starch and/or a modified high amylose starch
- b) from 4 to 13% by weight of a water soluble polymer selected from polyvinyl alcohol, polyvinyl acetate and copolymers of ethylene and vinyl alcohol which have a melting point compatible with the molten state of the starch components
- c) from 10 to 35% by weight of a polyol plasticizer
- d) from 0.5% to 10% of a polyethylene oxide or polyethylene glycol
- e) from 0 to 1.5% by weight of a $C_{12-22}$ fatty acid or salt and
- f) from 0.25% to 3% of a food grade emulsifier The compositions defined are suitable for forming injection moulded products including medical devices such as urine sample collectors and tampon applicators. The upper limit to the content of the modified starch is determined by its cost. This component contributes structural benefits to the resulting material including good cohesive and elongational properties, good optical properties, and resistance to retrogradation. The term retrogradation has been applied to describe the return to crystallinity by the starch components during storage after the heating and cooling operations. This process is what is generically referred to as staling and explains the hardening (or stiffening) of starch-based foods during extended storage. Hydroxypropylation helps to inhibit crystallinity. Typical modified starches include those having an hydroxyalkyl $C_{2-6}$ group or starch modified by reaction with an anhydride of a dicarboxylic acid. A preferred component is hydroxypropylated amylose. Other substituents can be hydroxyethyl or hydroxybutyl to form hydroxyether substitutions, or anhydrides such as maleic phthalic or octenyl succinic anhydride can be used to produce ester derivatives. The degree of substitution (the average number of hydroxyl groups in a unit that are substituted) is preferably 0.05 to 2. The preferred starch is a high amylose maize starch. A preferred component is a hydroxypropylated high amylose starch A939 marketed by Penford Australia. The minimum level of hydroxypropylation used is 6.0%. Typical values are 6.1 to 6.9%.

For cost savings and for property optimisation reasons one may substitute part of this starch with:
1) Higher or lower levels of hydroxypropylation
2) A higher level of unmodified starch. This may be possible in particular if the level of hydroxypropylation of the modified starch is increased;
3) A starch modified with octenyl succinic anhydride (OSA), which has a higher degree of hydrophobicity. The addition of this modified starch increases water resistance with increasing degree of substitution. The acetyl linkages in the OSA starch ensure that the material retains biodegradability upon access to water and a biologically active environment.

4) A starch co-polymer, preferably consisting of a styrene butadiene grafted with starch. This material improves impact resistance of the product.

The other starch component is any commercially available starch. This may be derived from wheat, maize, potato, rice, oat, arrowroot, and pea sources. Generally the moisture content (wet basis) is about 5 to 15%. Unmodified starch is a cheap biodegradable raw material from renewable resources that contributes to the barrier properties of the final product, therefore highly attractive for this to application. However, its use is limited by the occurrence of retrogradation (crystallisation resulting in brittleness), limited optical clarity of the resulting formed products, limited film-forming properties and limited elasticity for stretching. High-amylose starch is less sensitive to retrogradation (because it is found to be predominantly associated with the crystallization of Amylopectin within the cooked starch). A preferred concentration range for unmodified starch as a fraction of the total amount of starch is 0 to 50%.

The polymer component b) of the composition is preferably compatible with starch, water soluble, biodegradable and has a low melting point compatible with the processing temperatures for starch. Polyvinyl alcohol is the preferred polymer but polymers of ethylene-vinyl alcohol, ethylene vinyl acetate or blends with polyvinyl alcohol may be used. Water solubility of the selected polymer should preferably not occur at room temperature conditions. PVOH offers a combination of excellent film forming and binder characteristics, good elasticity and aids processing of starch-based formulations. PVA (Polyvinyl Alcohol) is produced by the hydrolysis of polyvinylacetate which is made by the polymerization of vinyl acetate monomer. The fully hydrolyzed grades contain few, if any, residual acetate groups; while partially hydrolyzed grades retain some of the residual acetate groups. Fully hydrolyzed grades dissolve in hot (200° F.) water, and remain in solution when cooled to room temperature. Preferred grades of PVOH include DuPont Elvanol 71-30 and Elvanol 70-62. Their properties are listed in Table 1.

TABLE 1

Properties of PVOH grades used in this invention

| | Grade | |
|---|---|---|
| | 71-30 | 70-62 |
| Weight Average MWt | 93,700 | 107,000-112,000 |
| Intrinsic viscosity (mPa · s) | 27-33 | 58.0-68.0 |
| Hydrolysis (%) | 99.0-99.8 | 99.4-99.8 |

The higher molecular weight grade appears to reduce brittleness and potentially also water sensitivity. The maximum level is mainly determined by costs. Increasing the level of PVOH significantly decreases Young's modulus. Film forming may be difficult below 6%. A preferred concentration range for injection moulding material is 6 to 13%.

The preferred plasticiser is a mixture of polyols, in particular sorbitol, and one or more other polyols particularly maltitol, glycerol, mannitol and xylitol, although erythritol, ethylene glycol and diethylene glycol are also suitable. The plasticizer plays a triple role: it provides suitable rheology for the extrusion compounding process and for the injection moulding process whilst also positively affecting the mechanical properties of the product. Cost, food-contact or skin/mucosal membrane contact are important issues in choosing the appropriate plasticizer. Processing performance, mechanical properties and shelf life of the end product depend on the exact composition of the polyol mixture. At zero or very low water content, the plasticizer content is preferably 10% to 35%, more preferably 20%. Dependent on the type of plasticizer(s) used, the equilibrium moisture content of the injection moulded product, as measured by standard moisture balance method, is around 2-5%.

Sorbitol, Maltitol and Glycerol blends are particularly suitable for modifying the mechanical properties of the formulation, as is Xylitol and blends of Xylitol with Sorbitol and Glycerol. Sorbitol and Xylitol are particularly good humectants. However, when using Glycerol in particular below a certain threshold, an anti-plasticisation may occur, where due to the temporary increased mobility of the polymer chains due to the presence of the plasticiser, crystallisation or at least a high degree of ordering may occur causing an increased stiffness and brittleness of these formulations compared to the un-plasticised starch formulation. Furthermore crystallisation is observed when Sorbitol is used on its own. Some polyols (Sorbitol and Glycerol in particular) may exhibit migration to the surface, where either an opaque crystalline film may form in the case of Sorbitol, or an oily film in the case of Glycerol. Blending various polyols inhibits this effect to varying degrees. Stabilisation may be enhanced with the addition of glycerol monostearate and sodium stearoyl lactylate as emulsifiers. Furthermore, synergistic effects with salt result in stronger effects on mechanical properties.

An alternative plasticiser is epoxidised linseed oil at 5% to 10%. This plasticiser, preferably stabilised with an emulsifying system aids processing but does not result in a significant further reduction in Young's modulus.

Water is present during the compounding process to ensure appropriate starch gelatinization. Excess water may be removed during compounding by means of to venting or on/off line pellet drying, and may be further regulated to desired levels prior to injection moulding by means of e.g. hopper drying. The humectant properties of the selected blend of polyols will dictate the suitable and stable moisture content of the product. Depending on the polyol blend utilized, the plasticizer content is preferably 10 to 35% and the water content is 10 to 0%. For highly flexible injection moulding components the plasticizer content is preferably higher than for rigid injection moulding or sheet products.

The polyethylene oxide and polyethylene glycol alternately or together ensure that the composition is biocompatible and can be used in medical devices that have contact with mucosal tissues, including urine sample collectors and tampon applicators. The preferred polyethylene oxide is one having a molecular weight above 20,000. For medical applications the formulations must pass Cytoxicity (ISO 10993-5), Sensitisation (ISO 10993-10) and Irritation (ISO 10993.10) tests. A preferred additive is Polyethylene oxide (PEG-5000 with a Mw of 210,000) added at 0.57% or 2% instead of stearic acid results in zero lysis in the cytoxicity test and when added at 5% in addition to stearic acid at 0.57% it also results in zero lysis.

Polyethylene oxide and polyethylene glycol alternately or together furthermore provide an increased water resistance to the formulation, to prevent excessive swelling which may result in delamination in particular in multi-layer structures (MLS).

The fatty acid or fatty acid salt component is preferably present in concentrations of 0.5 to 1.5%. Stearic acid is the preferred component. Sodium and potassium salts of stearic acid can also be used. Again cost can be a factor in the choice of this component but lauric, myristic, palmitic, linoleic and behenic acids are all suitable. Stearic acid is preferred as a lubricating agent because it has shown better compatibility with starches. As well as stearic acid, the salts such as calcium stearate may be used. The stearic acid appears to migrate to the surface of starch-based polymers.

It is thought that starch may form complexes with fatty acids. The starch glucopyraniside (glucose) is a six-membered ring in the "chair" configuration. The perimeter of the ring is hydrophilic, while the faces are hydrophobic. The starch chain forms a helix, with about six residues per turn. The result is a hollow cylinder with a hydrophilic outer surface and a hydrophobic inner surface. The inner space to is about 4.5 Å in diameter and straight chain alkyl molecules like stearic acid can fit into it. In the same manner, the fatty acid part of emulsifiers such as GMS can form a complex with gelatinized starch, retarding starch crystallization, thereby slowing the process of staling. The amount of monoglyceride that complexes with amylose (the linear component in starch) and with amylopectin (the branched component in starch), is dependent upon the degree of saturation of the fatty acid portion of the emulsifier. Unsaturated fatty acids have a bend produced by the double bond in the fatty acid chain that limits their ability to form a complex. Stearic acid is particularly useful as a processing aid, however in the presence of PEO or PEG it may not be necessary. The choice of appropriate processing aid is largely limited by the required resistance to delamination in MLS.

The emulsifier is preferably a food grade emulsifier and assists in maintaining the lipid and hydrophilic components homogenously dispersed in the composition. Typically the selection is dependent on the HLB (hydrophilic lipophilic balance) value. The preferred emulsifiers are selected from food grade emulsifiers with HLB numbers between 2 and 10 and include Propylene glycol monostearate, Glycerol Monoleate, Glycerol monostearate, Acetylated monoglycerides (stearate), Sorbitan monooleate, Propylene glycol monolaurate, Sorbitan monostearate, Calcium stearoxyl-2-lactylate, Glycerol monolaurate, Sorbitan monopalmitate, Soy lecithin, Diacetylated tartaric acid esters of monoglycerides, Sodium Stearoyl lactylate, Sorbitan monolaurate. Sodium Stearoyl Lactylate and Glycerol Monostearate are commonly used in starch systems.

TABLE 2

Hydrophobic/Hydrophilic Balance (HLB) Values for some Emulsifiers

| Emulsifier | HLB Value |
|---|---|
| Sodium Stearoyl Lactylate (SSL) | 21.0 |
| Polysorbate 80 (Sorbitan Monooleate) | 15.4 |
| Polysorbate 60 (Sorbitan Monostearate) | 14.4 |
| Sucrose Monostearate | 12.0 |
| Polysorbate 65 (Sorbitan Tristearate) | 10.5 |
| Diacetyl Tartaric Ester of Monoglyceride (DATEM) | 9.2 |
| Sucrose Distearate | 8.9 |
| Triglycerol Monostearate | 7.2 |
| Sorbitan Monostearate | 5.9 |
| Succinylated Monoglyceride (SMG) | 5.3 |
| Glycerol Monostearate (GMS) | 3.7 |
| Propylene Glycol Monoester (PGME) | 1.8 |

Glycerol monostearate added at levels ranging from 1-1.5% acts as an emulsifier to stabilise mechanical properties and increase homogeneity of the blend. Sodium Stearoyl Lactylate at 0.25% to 1.5% added to a plasticiser system further stabilizes mechanical properties and increases homogeneity of the blend. Stearoyl Lactylate (as the sodium or calcium salt) is also commonly used as a dough strengthener and may hence act as an anti-retrogradation agent. Combinations of glycerol monostearate and sodium stearoyl lactylate result in faster stabilisation of properties. The HLB value follows the additive rule and is of order 4 to 10 for a suitable mixture of SSL and GMS.

Water is added for the purpose of "gelatinising" (also called destructurising or melting) the starch into a polymeric gel structure. Water also may act like a plasticiser in the end-product in that it softens the material or reduces the modulus. The moisture contents of the material may vary at water activities or relative humidities (RH) below 30% or superior to 75%. In many applications, the local RH to which the material is exposed may reach values of up to 90%. For stable mechanical, lamination properties and for ease of processing at all temperatures, non-volatile plasticisers are preferred. Therefore some or all of the water may be dried off during or after the compounding stage and/or in the feeding stage of the subsequent injection moulding or film forming. This may be achieved with venting the extruder barrel, and/or on-line drying of the pellets. Extrusion processing of unplasticised formulations is possible with water concentrations as low as 10% and formulations with Polyol plasticisers may be dried to 0% free water before injection moulding. The preferred moisture content is the equilibrium moisture content of the formulation at the in-use RH range of the end product as determined by moisture sorption experiments. This depends on the specific composition of the formulation but is in the range of 3-12%.

For a tampon applicator a more preferred formula on a dry weight basis is
a) from 50 to 70% by weight of starch, of which 50-100% is modified
b) from 5 to 13% by weight of a water soluble polymer selected from polyvinylacetate, polyvinyl alcohol and copolymers of ethylene and vinylalcohol which have a melting point compatible with the molten state of the starch components
c) from 15 to 35% by weight of a polyol plasticizer
d) from 0.5 to 5% of a polyethylene oxide of molecular weight above 20,000
e) from 0 to 1% by weight of a $C_{12-22}$ fatty acid or salt and
f) from 0.25% to 1.5% of a food grade emulsifier
The moisture content of the tampon applicator is about 2 to 4%.

DETAILED DESCRIPTION OF THE INVENTION

A preferred formulation will be described with reference to a preferred application of the formulation to products such as tampon applicators which need to be injection moulded in large quantities and be inexpensive, disposable by means of the waste water system (e.g. flushing), suitable for food contact or medical devices and biodegradable. Formulations meeting all these criteria are not currently available in the market.

Tampon applicators are usually made by injection moulding low density polyethylene (LDPE) in a multi cavity tool typically with more than 100 cavities. Tampon applicators are usually a two part product comprising a barrel with an optional rounded tip consisting of flexible wings that open up when the tampon is pushed forward and an inner plunger which are assembled with the tampon and packed in flow wrap. The typical desirable mechanical properties for the polymer to be used in a tampon applicator are Young's modulus less than 400 MPa, elongation at break greater than 30% and tensile stress at break greater than 10 MPa. The applicator should not show instantaneous tackiness on contact with water and should be resistant to mould growth.

A preferred tampon applicator contains 55 to 65% of hydroxypropylated high amylose starch; 11 to 13% polyvinyl alcohol; 18 to 21% of a polyol mixture containing sorbitol, and at least two of maltitol, glycerol and xylitol; 1.5 to 2.5% of polyethylene oxide with a molecular weight in the range of 100,000 to 400,000; 0.5 to 1.5% of glycerol monostearate and sodium stearoyl lactylate; 0.7 to 0.9% of stearic acid.

Based on cost and performance considerations a suitable formulation for a tampon applicator is (on dry and wet basis):

TABLE 3

| Hydroxy propylated high-amylose starch | Polyol plasticizer mixture | PVOH | PEO | Glycerol monostearate | Stearic Acid | Sodium stearoyl lactilate | Moisture Content |
|---|---|---|---|---|---|---|---|
| 63.5% | 19.8% | 12.7% | 1.98% | 0.99% | 0.79% | 0.25% | Dry basis |
| 62.8% | 19.6% | 12.6% | 1.96% | 0.98% | 0.78% | 0.25% | 3% Injection moulding product |
| 58.36% | 18.2% | 11.7% | 1.82% | 0.91% | 0.73% | 0.23% | 10% max granulate moisture content |

Figure 5:
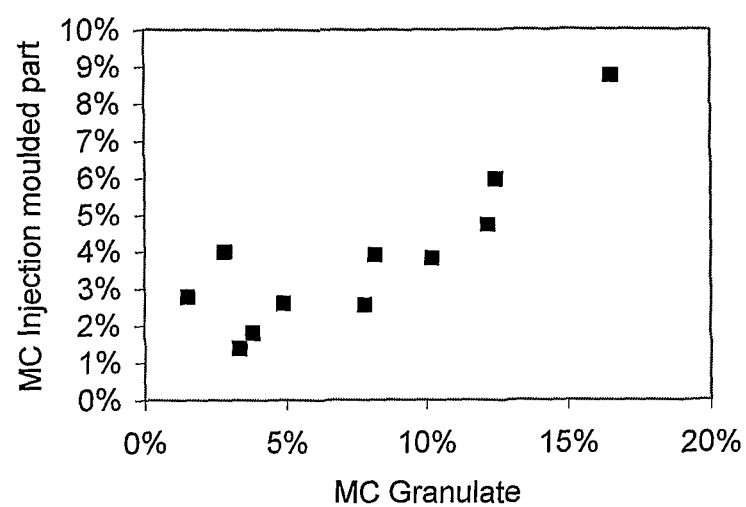
FIG. 5 illustrates the equilibrium moisture content of injection moulded tensile bars as a function of granulate moisture content.

In this formulation the polyol composition is preferably [Sorbitol]>2-[Maltitol] a [Glycerol]. Dependent on the composition of plasticizer(s) used, the equilibrium moisture content of the injection moulded product, as measured by standard moisture balance method, is of order 2-5%, see FIG. 5. This equilibrium is reached within 24 h, or even instantly after processing, as long as the granule moisture content is below 10%. This formulation has a Young's modulus of 197 MPa, a stress at break of 15.2 MPa, and an elongation at break of 113%.

The applicators are biodegradable and have strength and flexibility properties comparable to the non biodegradable materials currently used. The costs of production are also comparable.

The material is manufactured by means of extrusion compounding, using co- or counter-rotating twin screw or selected design single screw extruders. The preferable process is twin screw co-rotating compounding, with an extrusion pressure of at least 20 Bar and with a screw speed of at least 100 RPM. Water may be added to the process (by means of liquid injection together with the plasticisers) dependent on the level and nature of other plasticisers. Removal of water may be carried out by means of convective drying for the extrudate strands, a centrifuge and a fluidised bed for granulate, or barrel venting or both. Granulate may be obtained by means of underwater pelletising, die face cutting or strand cooling and cutting.

A suitable process involves compounding and injection moulding in tandem, where the extrudate is accumulated in a shooting pot and injected into the mould. Here the injection moulder inlet moisture content is optimised for best processing conditions and minimal shrinkage.

If required, further drying of the injection moulded parts may occur in a drying tunnel, drum, or fluidised bed.

The material may be injection moulded using conventional screw driven or injection driven processes with hot or cold runner systems. The viscosity of the formulation given above is comparable or lower than that of LDPE at shear rates typical for the injection moulding process. This means that pressures for multi-cavity processing will be comparable to the conventional process. For single-cavity injection moulding conditions for selected formulations of this invention, injection pressures are of order 50-500 Bar, barrel temperatures 90-180° C., nozzle temperature 80-120° C., mould temperature 25-90° C. The other key aspect affecting injection moulding efficiency is cycle time which is dominated by the time taken for the part to become sufficiently solidified after moulding. The low processing temperature for the formulations of this invention, and the absence of an actual molten state, results in short solidification time, hence short cycle time comparable to polyethylene. This makes the formulation suitable for high volume injection moulding operations.

CONTROL EXAMPLE

To illustrate how the formulations of this invention achieve properties specific for the application of this invention, the listed Examples are compared to a Control example which is a biodegradable starch-PVOH based material suitable for thermoforming applications, described in patent specification to WO00/36006.

Example 1

A formulation was developed which contained the same grades and relative proportions of starch, PVOH and stearic acid as the "Control" formulation but 23% plasticizer (on dry basis). The plasticizer system consist of a mixture of glycerol, maltitol and sorbitol in the ratios 3.3:1.5:1. In addition this formulation contains 1% of a polyethylene oxide for biocompatibility and 1.7% glycerol monostearate as emulsifier. It meets all the mechanical property requirements for the tampon applicator, as illustrated in Table 5.

Example 2

The second formulation is identical to Example 1 with the exception of the composition of the plasticizer, which consists of glycerol, maltitol and sorbitol in ratios 4.3:1:3.5. This significantly higher sorbitol level results in a higher Young's modulus as illustrated in Table 4.

Example 3

The Control formulation is not suitable for tampon applicators, because it fails the Cytotoxicity test required to ensure biocompatibility to the level required of a medical device class IIA. In this Example, stearic acid which is instrumental in the cytotoxicity was removed and PEO added at a level of 0.6%.

Example 4

Also developed to verify the determining factors in cytotoxicity, this Example has a 5.5% level of PEO, whilst maintaining the same level of stearic acid as the Control formulation.

Example 5

For comparative purposes with the Control, Example 3 and Example 4 this formulation contains no stearic acid, and a 2% level of PEO. The biocompatibility of these formulations is discussed later and tabulated in table 8. Furthermore this formulation is comparable to Example 2, except for a higher level of PVOH. The ratio PVOH to (dry) starch is 0.20 compared to a ratio of 0.11 for Example 2

Figure 3:
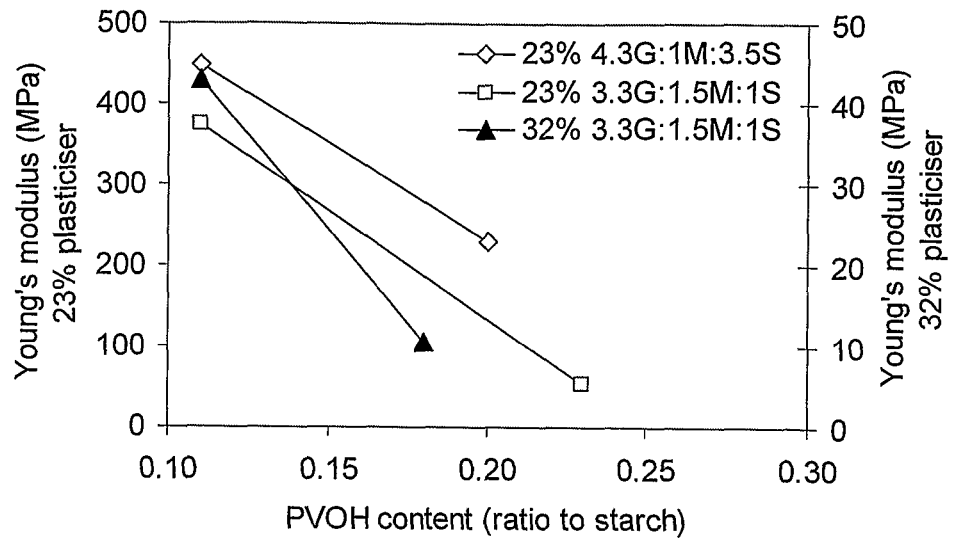
FIG. 3 illustrates the Young's modulus as a function of amount of PVOH.
Figure 4:
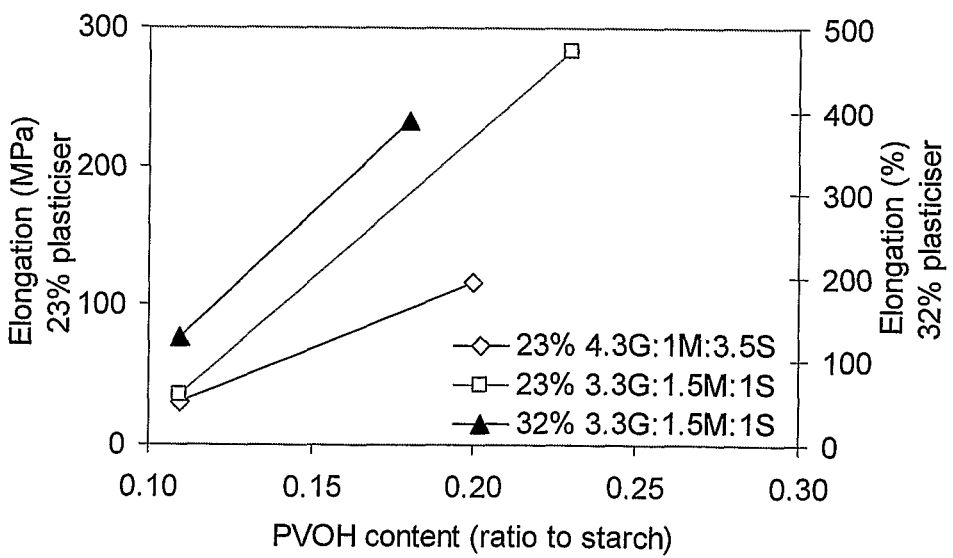
FIG. 4 illustrates the Elongation at break as a function of amount of PVOH.

This results in a significant reduction in Young's modulus, and a significant increase in elongation at break, as illustrated in FIG. 3 and FIG. 4 respectively and in Table 4.

Example 6

This formulation is plasticized to 21% with the Glycerol, Maltitol, Sorbitol, mixture of Example 1. It contains an emulsifier system of 1% GMS and 0.28% SSL, and 0.5% PEO. It meets all the mechanical property requirements for the tampon applicator, as illustrated in Table 5.

Example 7

This formulation is comparable to Example 1, except for a higher level of PVOH. The ratio PVOH to (dry) starch is 0.23 compared to a ratio of 0.11 for Example 1. This results in a significant reduction in Youngs modulus, and a significant increase in elongation at break, as illustrated in FIG. 3 and FIG. 4 respectively and in Table 4.

Example 8

This formula is plasticised to 32% with the polyol mixture of Example 1. The higher level of plasticization significantly reduces the Young's modulus, the is tensile strength, and increases elongation at break dramatically. The properties are stabilized with a GMS/SSL mixture at 1% and 0.25% respectively, and cytotoxicity is overcome by 1% PEO.

Example 9

Figure 2:
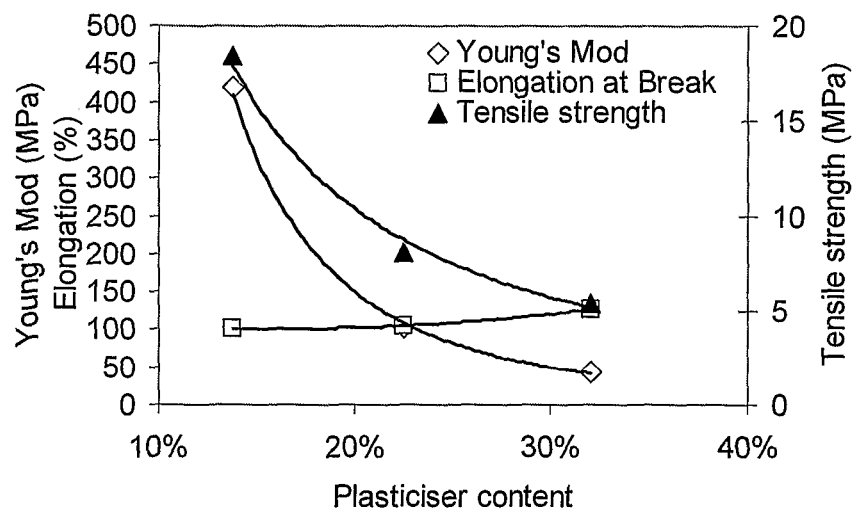
FIG. 2 illustrates mechanical properties as a function of the amount of plasticiser.

The following three examples were developed to quantify the dependence of mechanical properties on the level of plasticizer used, illustrated in FIG. 2 and, Table 4. The plasticizer polyol mixture is that of Example 1. This formula contains 14% plasticiser. The GMS/SSL emulsifier is incorporated at a 0.3%/0.1% level, PVOH at the same ratio as the Control example and no PEO is added.

Example 10

This formula has the same PVOH/Starch ratio, and the same type and level of emulsifier, and the same type of plasticizer as Example 9, but with a plasticizer level of 23% instead of 14%. At the equilibrium 4% moisture content, the resulting tensile test bars meet all the mechanical property requirements for the tampon applicator, as illustrated in Table 5.

Example 11

This formula has the same PVOH/Starch ratio, and the same type and level of emulsifier, and the same type of plasticizer as Example 9, but with a plasticizer level of 32%. This formulation is also comparable to Example 8, except for a lower level of PVOH. The ratio PVOH to (dry) starch is 0.11:1 compared to a ratio of 0.18 for Example 8. This results in a significant reduction in Young's modulus, and a significant increase in elongation at break, as illustrated in FIG. 3 and FIG. 4 respectively, and in Table 4.

Example 12

Figure 1:
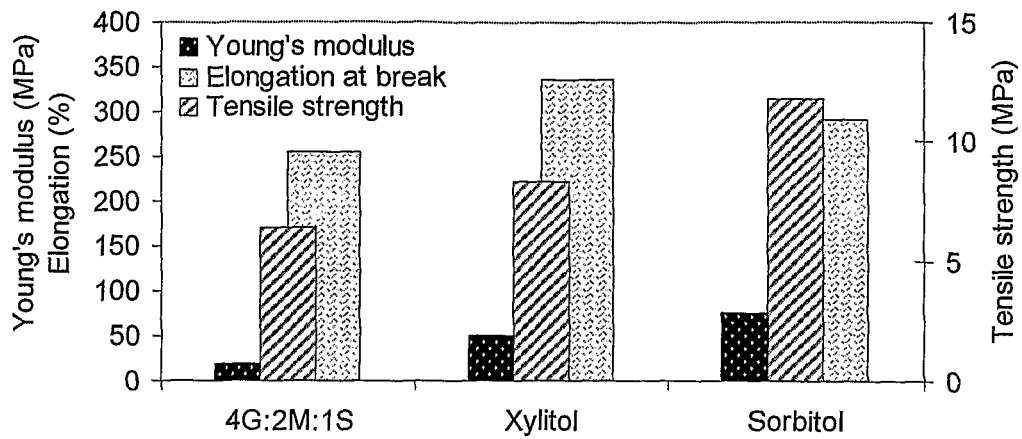
FIG. 1 illustrates mechanical properties as a function of the type of plasticiser.

The following four examples were developed to quantify the dependence of mechanical properties on the type of polyol plasticizer used, illustrated in FIG. 1 and table 4. The GMS/SSL emulsifier is incorporated at a 1%/0.25% level. The PVOH to starch ratio is 0.21, and no PEO is added. Each of the four formulas contains 35% plasticizer (on dry basis). The plasticizer polyol mixture in this formuation consists of a Glycerol, Maltitol, Sorbitol mixture with ratios 4:2:1. As discussed later and tabulated in table 6, these formulations show a different humectant behaviour, which is believed to be instrumental in the mechanical properties and their stability.

Example 13

To compare polyol plasticizers this material contains 35% Sorbitol. Sorbitol is the strongest humectant of the three compared plasticizer systems, resulting in the lowest moisture loss measurement at 130° C. as shown in Table 6. The humectant behaviour as well as the higher melting temperature of Sorbitol results in the highest Young's modulus, as illustrated in FIG. 1. It meets all the mechanical property requirements for the tampon applicator, as illustrated in Table 5. However, pure sorbitol exhibits a bloom effect, causing an opaque white crystalline layer on the injection moulded object surface, which may be eliminated by mixing sorbitol with minor amounts of maltitol and glycerol as in the preferred formulation of this invention.

Example 14

To compare polyol plasticizers this material contains 35% Xylitol.

Example 15

To compare polyol plasticizers this material contains 35% Glycerol.

Advantageous properties of this formulation that make it particularly suitable for ISO standard 10993 class 2A medical devices such as tampon applicators are:
1. Low Youngs Modulus (<400 MPa)

The stiffness of the material may be manipulated with the level and composition of polyol plasticiser and may range from 1145 MPa for unplasticised formulations, to 21 MPa for the examples with the highest levels of plasticiser. This makes these grades suitable for a wide range of injection moulding applications.

As shown in Table 4, using a range of plasticiser systems, the Youngs modulus (of compression moulded dogbones) has been reduced significantly from the base case formulation, which only contains water as plasticizer (Test method ASTM638).

as well as the plasticizer and emulsifier system used, and its humectant properties. Table 6 illustrates the superior humectant properties of the plasticizer system used in Example 13 (Sorbitol) and Example 14 (Xylitol) compared to Example 12 (mixture of glycerol>maltitol>sorbitol) and Example 15

TABLE 4

Mechanical properties of plasticised formulations

| Example | PVOH/ starch ratio | Emulsifier | | Plasticiser system (% wt on dry basis) | | | | PEO | Young's Modulus (MPa) | Tensile strength (MPa) | Elongation at break (%) |
|---|---|---|---|---|---|---|---|---|---|---|---|
| | | GMS | SSL | Glycerol | Maltitol | Sorbitol | Other | | mean (stdev) | | |
| control | 0.12 | | | | | | | | 1145 (143) | 24.8 (4.5) | 29.2 (5.1) |
| 1 | 0.11 | 1.7% | | 13% | 6% | 4% | | 1% | 375 (12) | 9.6 (0.3) | 36 (10.7) |
| 2 | 0.11 | 1.7% | | 11% | 2.6% | 9% | | 1% | 449 (13) | 10.5 (0.5) | 30.1 (8.5) |
| 5 | 0.20 | 1.1% | | 11% | 2.6% | 9% | | 2% | 230 (16) | 6.9 (0.1) | 117 (7.3) |
| 6 | 0.12 | 1.1% | 0.28% | 12% | 5% | 3.5% | | 0.5% | 111 (6.2) | 11.1 (0.8) | 186 (24) |
| 7 | 0.23 | 1.1% | | 13% | 6% | 4% | | 2% | 53.6 (6.5) | 8.8 (0.5) | 284 (38) |
| 8 | 0.18 | 0.9% | 0.23% | 19% | 8% | 6% | | 1% | 10.6 (1.2) | 4.5 (0.1) | 389 (29) |
| 9 | 0.11 | 0.3% | 0.1% | 8% | 3.5% | 2% | | | 418 (2.3) | 18.4 (0.6) | 101.5 (5.1) |
| 10 | 0.10 | 0.3% | 0.1% | 13% | 6% | 4% | | | 103 (11) | 8.1 (0.4) | 105 (5.4) |
| 11 | 0.11 | 0.3% | 0.1% | 18% | 8% | 5% | | | 42.9 (7.6) | 5.4 (0.2) | 127 (7.6) |
| 12 | 0.21 | 1.0% | 0.25% | 20% | 10% | 5% | | | 19.3 (1.5) | 6.4 (0.3) | 254 (34) |
| 13 | 0.21 | 1.0% | 0.25% | | | 35% | | | 74.5 (5.9) | 11.8 (0.2) | 291 (22) |
| 14 | 0.21 | 1.0% | 0.25% | | | | Xylitol 35% | | 49.4 (5.5) | 8.3 (0.3) | 336 (20) |

2. Strain at Break (>30%)

The extensional behaviour of the material may be manipulated with the level of plasticiser and may range from 37% minimum, for unplasticised formulations, to nearly 300% for the examples with the highest levels of plasticiser and PVOH. This makes these grades suitable for a wide range of injection moulding applications.

3. Tensile Strength (>10 MPa)

The tensile strength of the material may be manipulated with the level of plasticiser and may range from 4.5 MPa for highly plasticised formulations to 25 MPa for the examples with low levels or zero plasticizer. Hence, grades may be prepared suitable for a wide range of injection moulding applications.

Table 5 summarises the formulations that meet all the mechanical property requirements simultaneously. Here the listed moisture contents is measured using a Perkin lemer HB43 moisture balance at 130° C. after conditioning the specimens for 40 h as per ASTM638.

TABLE 5

Formulas that meet mechanical requirements for tampon applicator

| Example | MC (%)[1] | Young's Modulus (MPa) mean (stdev) | Tensile strength (MPa) mean (stdev) | Elongation at break (%) mean (stdev) |
|---|---|---|---|---|
| Example 1 | 3.0% | 390 (12) | 9.6 (0.3) | 50.1 (3.2) |
| Example 6 | 2.5% | 196 (15) | 11.1 (0.8) | 138 (18) |
| Preferred formula | 3.3% | 197 (25) | 15.2 (2) | 113 (9.5) |
| Example 10 | 1.8% | 130.6 (22) | 10.0 (0.5) | 169 (13) |
| Example 13 | 1.4% | 133 (10) | 11.8 (0.2) | 171 (13) |

An issue with starch-based polymers has been in the past that mechanical properties alter over time, as a result of moisture loss and/or crystallisation effects. Many of the compositions developed here show sustainable, non-hardening, mechanical properties. The time required for reaching equilibrium properties depends on the drying stages in the process (Glycerol). The table shows the measured moisture contents by means of a halogen moisture balance at 130° C., compared to the actual water content in the compounded formulas, which were not dried for the purpose of this test.

TABLE 6

Moisture loss at 130° C. of undried granulates with different humectant composition

| Example | Plasticiser at 35% | Moisture content in compounded formula (%) | Measured moisture loss (%) |
|---|---|---|---|
| Example 12 | Glycerol/Maltitol/ Sorbitol | 17.58% | 16.55% |
| Example 13 | Sorbitol | 18.82% | 5.53% |
| Example 14 | Xylitol | 20.13% | 7.83% |
| Example 15 | Glycerol | 18.76% | 16.72% |

A combination of barrel venting and granulate drying is recommended to reach equilibrium moisture content in the injection moulded part on-line. Formulations made without granulate drying/venting show a significant hardening within the first 100 h. Any subsequent hardening would then be due to crystallisation and/or antiplasticisation effects. Formulations with the preferred polyol composition processed at the appropriate moisture contents do not show aging of mechanical properties, as shown in Table 7. Any observed changes do not follow repeatable trends across the Examples, and are most likely due to the small sample size and the experimental scale of the part manufacture.

TABLE 7

Mechanical property stability as function of storage conditions

| | Example 9 | | Example 10 | Example 11 |
|---|---|---|---|---|
| Temperature | 23° C. | 37° C. | 23° C. | 37° C. |
| Time lapse | 2 months | 3 weeks | 2 months | 3 weeks |
| Change in Tensile Strength (MPa) | 2.80 | 0.17 | 1.01 | −0.49 |

TABLE 7-continued

Mechanical property stability as function of storage conditions

|  | Example 9 | Example 10 | Example 11 |
|---|---|---|---|
| Tensile Strength (% change) | 18% | 2% | 14% | −13% |
| Change in Elongation at Break (%) | 2.53 | −4.12 | −13.0 | 11.4 |
| Elongation at Break (% change) | 3% | −3% | −11% | 10% |

4. Shrinkage Comparable to Conventional LDPE

Shrinkage of injection moulded tensile test bars was observed. Many formulations showed comparable or lower shrinkage than for LDPE, even before any process to optimisation. Others showed higher shrinkage and would require further optimization, but shrinkage behaviour was found controllable for all grades.

| Example | Shrinkage (machine direction) |
|---|---|
| Example 6 | 6.6% ± 1.3% (N = 11) |
| Example 12 | 4.5% ± 0.5% (N = 40) |
| Example 14 | 2.9% ± 0.4% (N = 9) |
| Example 13 | 2.6% ± 0.2% (N = 10) |

5. Biodegradable

The compositions of this invention are biodegradable and compostable according to international standards, in particular EN13432:2000 for commercial composting facilities and waste water management systems. Biodegradation tests were carried out according to EN13432 requirements, in particular ISO 14855 in compost and ISO 14851 or ISO 14852 in aqueous medium. EN13432-specified disintegration tests demonstrated the required levels of disintegration in simulated conditions for commercial composting.

6. Flushable

The compositions of this invention disintegrate substantially in simulated conditions for waste water treatment and may therefore be considered flushable. Two example materials (control formula as a 1 mm thick sheet and formula Example 5 as a 1 mm thick injection moulded part) were tested for flushability in comparison to toilet paper.

For flushability testing, a modified version of standard method CEN TC 249 WI 249510 ("Plastics—Evaluation of disposability in waste water treatment plants—Test scheme for final acceptance and specifications") was used. Modifications to the method were: a) Sample drying was eliminated because complete drying of natural materials may change the microstructure and hence moisture sorption behaviour of the material; b) Different vessel and agitation conditions were used to better mimic the turbulent conditions experienced by flushed materials; c) The residue collected on the sieve was washed with excess water to better replicate the screening procedures at waste treatment plants. A 'flushability factor' was defined as the fraction of material that passes a 10 mm mesh sieve after 16 hours agitation in water.

It was found that both the Control and the formula of Example 5 achieved a flushability factor of 1.0, indicating that these materials may be considered flushable.

7. Biocompatible

Biocompatibility testing was conducted as required for medical devices of Class 2A according to ISO standard 10993 "Biological evaluation of medical devices". This class represents devices suitable for contact with mucosal membranes with single or multiple use or contact likely to be up to 24 h. Devices of this type must pass the following tests:

Cytotoxicity (ISO 10993-5)

With the use of cell culture techniques, these tests determine the lysis of cells (cell death), the inhibition of cell growth, and other effects on cells caused by medical devices, materials and/or their extracts. There are two methods that may be used to determine Cytotoxicity. One is the ISO Elution method, the other an Agar Overlay method. The former is a more sensitive test and was used for the evaluation of this invention.

Sensitisation (ISO 10993-10)

These tests estimate, using an appropriate model, the potential of medical devices, materials and/or their extracts for contact sensitization. These tests are appropriate because exposure or contact to even minute amounts of potential leachables can result in allergic or sensitization reactions. Sensitization tests are described in ISO 10993-10.

The formulations of this invention comply with this test.

Irritation (ISO 10993-10)

These tests estimate the irritation potential of medical devices, materials and/or their extracts, using appropriate sites for implant tissue such as skin, eye and mucosal membrane in a suitable model. Irritation tests are described in ISO 10993-10.

Biodegradable starch-PVOH material (Control) is not biocompatible, in that it fails to the cytotoxicity test, likely due to the effect of stearic acid which acts as a surfactant on the exposed cells. In order to ensure biocompatibility of the formulations of this invention, polyethylene oxide (or polyethylene glycol) was added at various levels and is shown to be effective both in the presence and absence of stearic acid. Table 8 summarises the formulation Examples that were is submitted to biocompatibility testing.

TABLE 8

Biocompatibility test results

| Example | Stearic acid (% wt dry basis) | PEO (% wt dry basis) | Cytotoxicity | Irritation | UPS Systemic toxicity |
|---|---|---|---|---|---|
| Control | 0.6% | 0% | fail | pass | pass |
| Example 3 | 0% | 0.6% | pass | Not carried out | |
| Example 4 | 0.6% | 5.5% | pass | | |
| Example 5 | 0% | 2.1% | pass | | |

The Cytotoxicity test was passed by the formulation Example 3, Example 4 and Example 5 of this invention (ISO Elution method IX Minimal Essential Media Extract (MEM) which is conducted at 37° C.). Furthermore, the Irritation test, and a USP systemic toxicity test in mouse, which was suggested to us as a screening test for the Sensitisation test, was passed by the control formulation of this invention, which does not include additives intended to increase biocompatibility, therefore it was not deemed necessary to test the biocompatibilised Example 3, Example 4 and Example 5.

8. Low cost.

The current formulations are significantly lower in cost than any biodegradable materials that meet some of the key criteria for this application, and not inhibitively more expensive to current non biodegradable or non-flushable tampon applicators (at most a factor 2-3 compared to current LDPE prices). This kind of formulation does not experience the level of price fluctuation that oil-derived polymers do.

The combination of low Young's modulus, high elongation at break, suitable tensile strength, biocompatibility, biodegradability, flushability and injection mouldability make these formulations ideally suitable for pharmaceutical and hygiene devices such as tampon applicators.

The performance and appearance of tampon applicators are acceptable and as good as conventional non-biodegradable applicators. Whilst not qualified at this stage, the material has a softer, more natural, feel than many conventional polymers. The significant advantage of the applicators made from the composition of this invention is that disposal is much simpler, more convenient and hygienic. From the above description and examples it can be seen that the present invention provides a biodegradable starch polymer that is comparable in price and performance characteristics to conventional non-biodegradable injection moldable polymers. Consequently tampon applicators can be just as presentable and attractive with the added benefit of being environmentally friendly.

Those skilled in the art will realize that although the present invention has been illustrated in relation to tampon applicators the injection moulding compositions of this invention can also be used for other applications by tailoring the specific composition content to the desired properties of the product. The composition may be used to mould other medical or food associated products, including cotton buds, urine collection aids, cutlery, scoops and spatulas where flushability and biodegradability are desirable. These properties also make the composition useful in products which currently represent a litter or waste management problem including toilet roll cores, toilet brush heads, clips and ties used in packaging, aesophagus clips used in meat processing, temporary sewer plugs in buildings, inert ammunition simulators, mosquito repellant buckets.

The invention claimed is:

1. A biodegradable injection mouldable polymer composition comprising, on a dry weight basis of total polymer composition:
   a) from 50 to 85% by weight of a starch and/or a modified high amylose starch;
   b) from 4 to 13% by weight of a water soluble polymer selected from the group consisting of polyvinyl alcohol and copolymers of polyvinyl alcohol/polyvinylacetate which have a melting point compatible with the molten state of the starch components;
   c) from 0.5 to 10% by weight of a polyethylene oxide polyethylene glycol;
   d) from 20 to 35% by weight of sorbitol and two or more other polyol plasticizers selected from the group consisting of glycerol, maltitol, xylitol, erythritol, mannitol, ethylene glycol, and diethylene glycol; and
   e) from 0.25 to 3% by weight of a food grade emulsifier.

2. The composition as claimed in claim 1 further comprising from 0 to 1.5% by weight of a $C_{12-22}$ fatty acid or salts thereof.

3. The composition as claimed in claim 2 in which the $C_{12-22}$ fatty acid or salts thereof is stearic acid.

4. The composition as claimed in claim 2 wherein component b) is a polyvinyl alcohol.

5. The composition as claimed in claim 1 wherein component b) is polyvinyl alcohol.

6. The composition as claimed in claim 5 in which component c) is a polyethylene oxide with a molecular weight in the range of 100,000 to 400,000.

7. The composition as claimed in claim 1 in which component c) is a polyethylene oxide with a molecular weight in the range of 100,000 to 400,000.

8. The composition as claimed in claim 1 in which the food grade emulsifier has a hydrophobic-lipophilic balance number of from 2 to 10.

9. The composition as claimed in claim 1 in which the food grade emulsifier is selected from the group consisting of glycerol monostearate, sodium stearoyl lactylate and mixtures thereof.

10. A medical device formed by injection moulding a composition as defined in claim 1 and which has a final moisture content of 2 to 3% by weight.

11. An injection moulded product comprising a composition as claimed in claim 1 which has a Young's modulus between 70 MPa and 400 MPa, a tensile strength between 8 MPa and 15 MPa and an elongation at break between 30 and 300%.

12. A tampon applicator made by injection moulding a composition comprising, on a dry weight basis of total composition:
   a) from 50 to 70% by weight of starch, of which 50 to 100% is modified;
   b) from 5 to 13% by weight of a water soluble polymer selected from the group consisting of polyvinyl alcohol and copolymers of polyvinyl alcohol/polyvinylacetate which have a melting point compatible with the molten state of the starch component;
   c) from 0.5 to 10% by weight of a polyethylene oxide polyethylene glycol;
   d) from 20 to 35% by weight of sorbitol and two or more other polyol plasticizers selected from the group consisting of glycerol, maltitol, xylitol, erythritol, mannitol, ethylene glycol, and diethylene glycol; and
   e) from 0.25 to 3% by weight of a food grade emulsifier.

13. The tampon applicator of claim 12 wherein the composition further comprises from 0 to 1% by weight of a $C_{12-22}$ fatty acid or salts thereof.

14. The tampon applicator as claimed in claim 13 which contains 55 to 65% by weight of an hydroxypropylated high amylose starch, 11 to 13% by weight polyvinyl alcohol, 20 to 21% by weight of a polyol mixture containing sorbitol, and at least two of maltitol, glycerol and xylitol, 1.5 to 2.5% by weight of polyethylene oxide with a molecular weight in the range of 100,000 to 400,000, 0.5 to 1.5% by weight of glycerol monostearate and sodium stearoyl lactylate, and 0.7 to 0.9% by weight of stearic acid.

15. The tampon applicator as claimed in claim 12 in which said tampon applicator has a moisture content of 2 to 4% by weight.

16. The tampon applicator as claimed in claim 12 which has a Young's modulus between 160 MPa and 200 MPa, a tensile strength of between 10 MPa and 15 MPa and an elongation at break between 50 and 150%.

17. The tampon applicator as claimed in claim 12 which is biodegradable in waste water and disintegrates so as to not negatively impact waste water management systems.

* * * * *

UNITED STATES PATENT AND TRADEMARK OFFICE
CERTIFICATE OF CORRECTION

PATENT NO. : 8,569,402 B2  
APPLICATION NO. : 11/664649  
DATED : October 29, 2013  
INVENTOR(S) : Henderson et al.

Page 1 of 1

It is certified that error appears in the above-identified patent and that said Letters Patent is hereby corrected as shown below:

IN THE CLAIMS:

Claim 1, Column 15, Line 47, "polyethylene glycol;" should read --or polyetheylene glycol;--.

Claim 12, Column 16, Line 33, "polyethylene glycol;" should read --or polyethylene glycol;--.

Signed and Sealed this  
Third Day of December, 2013

Margaret A. Focarino  
*Commissioner for Patents of the United States Patent and Trademark Office*

UNITED STATES PATENT AND TRADEMARK OFFICE
CERTIFICATE OF CORRECTION

PATENT NO.        : 8,569,402 B2  
APPLICATION NO.   : 11/664649  
DATED             : October 29, 2013  
INVENTOR(S)       : Henderson et al.

Page 1 of 1

It is certified that error appears in the above-identified patent and that said Letters Patent is hereby corrected as shown below:

IN THE CLAIMS:

Claim 1, Column 15, Line 47, "polyethylene glycol;" should read --or polyethylene glycol;--.

Claim 12, Column 16, Line 33, "polyethylene glycol;" should read --or polyethylene glycol;--.

This certificate supersedes the Certificate of Correction issued December 3, 2013.

Signed and Sealed this  
Thirty-first Day of December, 2013

Margaret A. Focarino  
*Commissioner for Patents of the United States Patent and Trademark Office*